United States Patent [19]
McLean

[11] 3,975,939
[45] Aug. 24, 1976

[54] METHODS OF AND APPARATUS FOR SIMULATING ULTRASONIC PULSE ECHOES

[76] Inventor: Archibald Joseph McLean, Rte. 2, Box 239 D4, Waldorf, Md. 20601

[22] Filed: July 2, 1975

[21] Appl. No.: 592,477

[52] U.S. Cl. .................................. 73/1 DV; 73/67
[51] Int. Cl.² ..................................... G01N 29/00
[58] Field of Search........... 73/1 DV, 67, 67.1, 67.2, 73/71.5 US; 340/5 C, 5 R, 8 R, 15

[56] References Cited
UNITED STATES PATENTS

| | | | |
|---|---|---|---|
| 2,796,756 | 6/1957 | Yates et al. | 73/1 DV |
| 2,966,057 | 12/1960 | Heller | 73/1 DV |

OTHER PUBLICATIONS

Rhodes, *Environmental Quarterly*, "Piezoelectric Transducer Calibration Simulation Method," 1962 pp. 1-4.

*Primary Examiner*—Richard C. Queisser
*Assistant Examiner*—Stephen A. Kreitman
*Attorney, Agent, or Firm*—Sherman & Shalloway

[57] ABSTRACT

Methods of and apparatus for simulating ultrasonic pulse echoes are used to test and calibrate ultrasonic flaw detectors by simulating a train of radio frequency pulses, having a pulse repetition frequency which is indicative of both the speed of sound in a material under test and the thickness of that material. This is accomplished by generating a train of d.c. pulses having a pulse repetition frequency, which is directly proportional to and, which is a multiple of the speed of sound of the material The pulse repetition frequency is also inversely proportional to the thickness of the material. The d.c. pulses are used to drive a radio frequency pulse generator and a pulse modulator. The outputs of the radio frequency generator and pulse modulator are then combined to produce a signal having an amplitude envelope, which simulates a series of ultrasonic pulse echoes.

9 Claims, 9 Drawing Figures

D.C. PULSES

FIG.1

FLAT-RF

FIG.2

LINEAR-RF

FIG.3

LOGARITHMIC-RF

METHODS OF AND APPARATUS FOR SIMULATING ULTRASONIC PULSE ECHOES

BACKGROUND OF THE DISCLOSURE

1. Field of the Invention

The instant invention relates to methods of and apparatus for simulating ultrasonic pulse echoes. More particularly, the present invention relates to methods of and apparatus for simulating ultrasonic pulse echoes, in order to test ultrasonic flaw detectors.

2. Technical Considerations and Prior Art

In order for ultrasonic flaw detectors to be reliable, it is necessary to test and calibrate the flaw detectors periodically to insure that the detectors have both horizontal and vertical linearity. If a flaw detector gives erroneous readings because of its own defects, it is impossible to determine whether or not an article or material being tested has flaws. Consequently, reliability of the flaw detector is of utmost importance in achieving reliability of the article or material being tested.

The usual method of testing and calibrating an ultrasonic flaw detector is to couple the transducer of the detector with standard test specimens, which have given thickness and sonic speeds. However, this procedure is rather time consuming and can be inaccurate, in that the tester must hold the transducer in contact with the test sample while the detector is being monitored.

Testing and calibrating detectors so that the detectors will correctly recognize flaws in an article consumes a great deal of time. This usually involves moving the transducer along a standard test sample having a plurality of holes positioned at different depths. The resulting signals decline logarithmically in amplitude and are then raised in amplitude by the flaw detector to a common level, in order to establish the linearity of the flaw detector. This test may take 10 to 15 minutes, and requires considerable manual effort.

When using the standard specimen approach, it is quite difficult to pin-point just where defects occur in the circuitry of the flaw detector. This test only indicates that there is something wrong with the flaw detector. However, the particular portion of the circuit in which the error occurs can not readily be identified, because the tester is not able to probe separate portions of the flaw detector circuit.

For these reasons, it is necessary to have a more convenient, more reliable and faster way of calibrating and testing ultrasonic flaw detectors.

OBJECTS OF THE INVENTION

Accordingly, it is an object of the instant invention to provide new and improved methods of and apparatus for testing and calibrating ultrasonic flaw detectors.

It is a further object of the instant invention to provide new and improved methods of and apparatus for testing and calibrating ultrasonic flaw detectors, which drastically reduce the time for testing and calibrating.

It is, still, another object of the instant invention to provide new and improved methods of and apparatus for testing and calibrating ultrasonic flaw detectors, wherein the testing time, generally, does not exceed 15 seconds.

It is, still, a further object of the instant invention to provide new and improved methods of and apparatus for testing and calibrating ultrasonic flaw detectors, wherein a single apparatus can simulate numerous test material conditions.

It is, still, another object of the instant invention to provide new and improved methods of and apparatus for testing and calibrating ultrasonic flaw detectors, wherein separate portions of the flaw detector circuitry may be monitored, in order to determine which portion is defective.

It is an additional object of the instant invention to provide new and improved methods of and apparatus for simulating ultrasonic pulse echoes.

It is, still, a further object of the instant invention to provide new and improved methods of and apparatus for simulating ultrasonic pulse echoes in a material of a given thickness and sonic speed by adjusting the frequency of an electronic clock accordingly.

SUMMARY OF THE INVENTION

In accordance with these and other objects, the instant invention contemplates a method of simulating an ultrasonic signal corresponding to a material under test by generating an initial pulse to start the simulation, and then generating a train of d.c. pulses, in response to the initial pulse. The pulse repetition frequency of the d.c. pulses is inversely proportional to the thickness of the material being simulated, and is directly proportional to the speed of sound in the material being simulated. A radio frequency pulse is then generated with each d.c. pulse, in order to produce a train of radio frequency pulses having a pulse repetition frequency equal to the frequency of the d.c. pulses. The train of radio frequency pulses is then modulated to produce a series of radio frequency pulses, which are selectively equal in amplitude, linearly declining in amplitude, or logarithmically declining in amplitude.

Apparatus for practicing the concepts of the instant invention may include a clock for generating a train of d.c. pulses, and controlling the frequency of the pulses, so that the pulse repetition frequency is directly proportional to the speed of sound of a material being simulated. The train of pulses is then applied through a frequency divider, which divides the frequency by a factor indicative of the thickness of the material. A radio frequency pulse generator is driven at the pulse repetition frequency of the d.c. pulses to produce a train of radio frequency pulses, which are subsequently modulated to produce trains of radio frequency pulses, which are selectively equal in amplitude, linearly declining in amplitude, or logarithmically declining in amplitude. The modulated radio frequency pulses simulate the electrical signal produced by an ultrasonic transducer monitoring a material, which has been ultrasonically excited.

DETAILED DESCRIPTION

In operation, ultrasonic flaw detectors process pulses, which are received from a transducer coupled to an article or material being tested. The pulses correspond to echoes, which are reflected back and forth through the thickness of the material with a constant velocity, and logarithmically or exponentially decreasing power. Generally, the pulses are created by a single impulse or "main bang," which is applied by the transducer or, perhaps, another transducer to the article.

If the article being tested is made of a homogeneous material and has a constant thickness, the pulse repetition frequency of the pulses generated by the echoes will be constant, because the speed of sound in the material is constant. In other words, since the sound wave must travel a fixed distance for each cycle of reflection, and the speed of the sound wave is constant, the interval of time between each reflection of the sound wave will be the same.

Referring now to FIGS. 1 through 4, there is shown a pulse model, which simulates the behavior of a sound wave being reflected in a material of constant thickness. In each of these figures, the pulses are equidistant from one another with respect to the time axis (the horizontal axis), thereby showing constant pulse repetition frequency.

Figure 1:
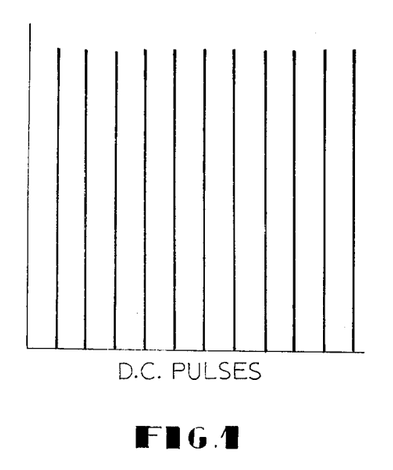
FIG. 1 is a schematic illustration of an ultrasonic flaw detector screen showing response to a train of constant amplitude d.c. pulses.

As seen in FIG. 1, there is a train of 11 spiked d.c. pulses of constant frequency. These pulses are of constant amplitude, because they are not meant to relate to anything but speed and distance, both of which are constant. If the material is changed in either substance or thickness, then the interval between the pulses will change. For example, if a material with a relatively high speed of sound is simulated, the pulses will move close together, because they will occur more frequently. If a material, which is relatively thick, is simulated, then the pulses will move further apart, because it will take longer for a sound wave to cycle in the material. It can be readily seen that for a given material, having a given constant thickness, the pulses can be spaced, so as to accommodate both the speed of sound in the material and the thickness of the material.

Figure 2:
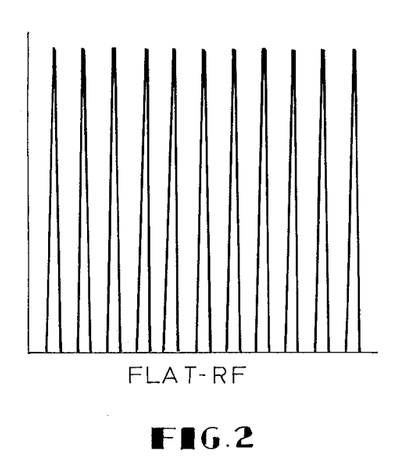
FIG. 2 is a schematic illustration of an ultrasonic flaw detector screen showing response to a train of radio frequency pulses having a constant amplitude.
Figure 3:
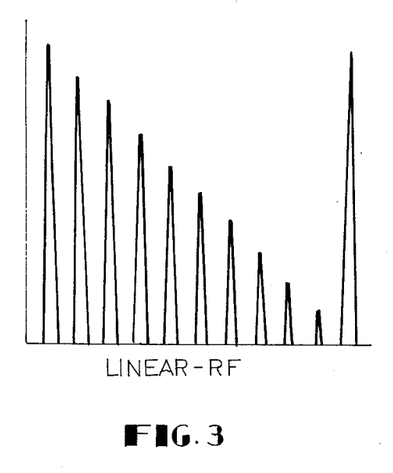
FIG. 3 is a schematic illustration of an ultrasonic flaw detector screen showing response to a train of radio frequency pulses, which are linearly declining in amplitude.
Figure 4:
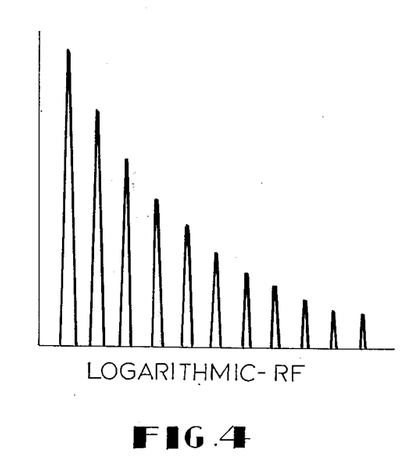
FIG. 4 is a schematic illustration of an ultrasonic flaw detector screen showing response to a train of radio frequency pulses, which are logarithmically or exponentially declining in amplitude.

Referring now to FIGS. 2, 3 and 4, there are shown trains of radio frequency pulses, which simulate the signal received and conveyed by a transducer monitoring a material of constant thickness. In each figure, the radio frequency pulses occur at a constant frequency. However, the amplitude envelopes vary according to the test being performed. As will be explained hereinafter, the radio frequency pulse trains are driven according to the pulse repetition frequency of the d.c. pulses, and are modulated in amplitude before being impressed on the ultrasonic flaw detector under test. The individual radio frequency pulses are configured to resemble the pulses produced by a gammatype transducer.

Referring now, specifically, to FIG. 2, there is shown a series of radio frequency pulses of constant amplitude. These pulses are used to test the horizontal linearity of an ultrasonic flaw detector. This is quite easily accomplished by shifting the series of pulses to the left and right, and observing whether or not the pulses remain equally spaced. Generally, this shift may be effected by adjusting the delay control of the flaw detector under test.

Referring now, specifically, to FIG. 3, there is shown a train of radio frequency pulses, which are linearly declining with the first pulse being the initial pulse, and each succeeding pulse being reduced by one horizontal scale division for each major vertical division. The eleventh pulse has the same full amplitude as the first pulse, and serves as a framing pulse. The train of pulses, shown in FIG. 3, is used to check the vertical linearity of an ultrasonic flaw detector.

Referring now, specifically, to FIG. 4, there is shown a train of radio frequency pulses, which decline in amplitude logarithmically. The first pulse simulates the initial pulse and each succeeding pulse is reduced by two decibels to achieve the logarithmic attenuation pattern. This signal can be used to test the decibel switch accuracy of the ultrasonic flaw detector under test. It is also useful in setting up the time delayed gain controls of an ultrasonic flaw detector.

Figure 5:
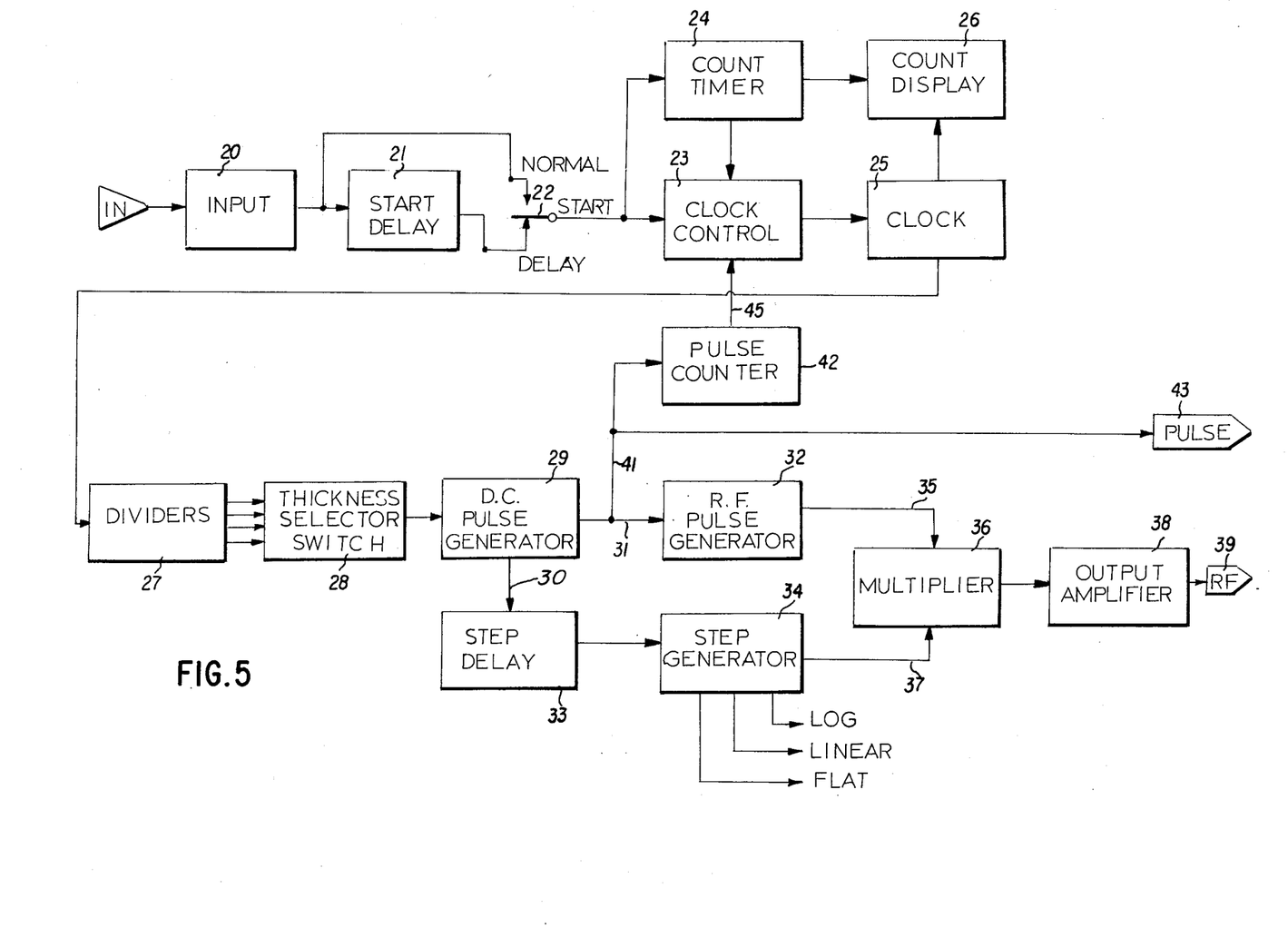
FIG. 5 is a block diagram generally showing how the apparatus of the instant invention is constructed and operated.

FIG. 5 — GENERAL OPERATION

Referring now to FIG. 5, there is shown a block diagram generally showing a circuit for practicing the principles of the instant invention. In operation, an input is received from the ultrasonic flaw detector under test in the form of a "main bang" pulse. The "main bang" pulse is the pulse which normally causes the transducer of the ultrasonic flaw detector to excite the material under test. However, in this case, the "main bang" is applied to the simulating circuit of FIG. 5, which is substituted for the transducer and the material with which the transducer is coupled.

The "main bang" is applied to an input 20 which generates the trigger pulse, that is compatible with the logic of the circuitry of FIG. 5. The input 20 is preferably capable of self-triggering, so as to produce a trigger pulse at a rate of approximately five times per second, in the absence of a "main bang" or input signal.

Generally, there are two types of tests, which are conducted by ultrasonic flaw detectors. In one type of test, the transducer of the flaw detector is coupled directly to the article or material under test. In the other type of test, the transducer is coupled to the article or material through a water path. Since the water path rather drastically reduces the velocity of the signal, while the signal is traversing the water path, it is necessary to introduce a delay, after the application of the "main bang" pulse. This delay simulates the sound wave traversing the water path. In order to simulate water paths of variable lengths, the delay itself is variable over a range of 12 to 45 microseconds. The delay apparatus is illustrated by the start delay box 21 and switch 22, which either bypasses the start delay box 21 by engaging the normal contact or includes the start delay box 21 by engaging the delay contact.

The trigger pulse is then applied simultaneously to a clock control 23 and a count timer 24. The clock control 23 then starts clock 25, which generates basic timing. The clock control also includes a velocity setting, which sets the clock frequency equal to a multiple of the speed of sound or acoustic velocity of the material being simulated. For example, the clock control may set the frequency of the clock at ten times the acoustic velocity setting. Generally, this will be a frequency of 1.1 to 2.6 Megahertz. As previously explained, the frequency of occurrence of an echo is directly proportional to the speed of sound or acoustic velocity of the material which is ultrasonically excited.

The clock has an output which operates a velocity display 26, which by a light-emitting diode display or the like, informs the operator of the speed or velocity being simulated. The count timer 24 controls the period over which the clock pulses are counted, for example 100 microseconds.

The clock 25 applies its output frequency to a frequency divider 27, which is controlled by a thickness-selector switch 28. As previously set forth, the frequency of an ultrasonic echo is inversely proportional to the thickness of the material excited. Consequently, the thicker the material is, the lower the frequency will be.

In operation, the thickness-selector switch and frequency divider first divide the clock frequency by 10 to produce a string of pulses equivalent to round trips in a half inch of material, in other words, a material with a total sonic path of one inch. In order to simulate other thicknesses, the pulses are further divided. For example, a 1-inch thickness of material requires further a division by two, a 10-inch thickness of material requires a further division by 20, and a 50-inch thickness of material requires a further division by 100.

The output from the frequency divider, as determined by the thickness selector switch, is applied to a d.c. pulse generator 29, which generates the d.c. pulse train shown in FIG. 1, that is directly proportional to the acoustic velocity of the material being simulated, and inversely proportional to the thickness of the material being simulated. The outputs of the d.c. pulse generator determine the pulse repetition frequency of the radio frequency pulses, which simulate echoes produced in a material by a gamma-type transducer.

One output from the d.c. pulse generator is applied over line 31 to a radio frequency pulse generator 32, while another output from the d.c. pulse generator is applied over line 30 through a step delay 33 and into a step generator 34. It is to be understood that the frequencies from the d.c. pulse generator applied over lines 31 and 30 are the same. The radio frequency pulse generator shapes the radio frequency pulse by adjusting electrical damping in resonant circuits so as to simulate mechanical damping in a transducer. The radio frequency pulse is applied over line 35 to a multiplier 36, which also receives a signal over line 37 from the step generator 34. There is a slight delay caused by the step delay 33 in the receipt of the signal from the step generator 34, in order that the multiplier will have passed a completely formed radio frequency pulse prior to receiving the next modulating signal level from the step generator 34.

The step generator 34 determines the amplitude of each pulse. In other words, if the step generator is operated in the log mode, successive pulses will be modulated to produce the logarithmic configuration of FIG. 4. If the step generator is in a linear mode, each successive pulse will be modulated according to a configuration of FIG. 3, and if the step generator is in the flat mode, each successive pulse will be the same as shown in FIG. 2.

From the multiplier 36, successive modulated radio frequency pulses are passed through an appropriate output amplifier, and impressed on the transducer lead of the flaw detector circuit by a suitable connector 39.

The pulses generated by d.c. pulse generator 29 and applied over line 31, are also applied over line 41 to a pulse counter 42 and a pulse terminal 43. The pulse counter 42 counts eleven pulses and then generates a pulse over line 45 to the clock control, which stops the clock from running until another start pulse is received. The terminal 43 is selectively coupled to a display device such as a cathode-ray tube and may also be coupled to the ultrasonic flaw detector to run pure pulse repetition frequency test.

FIGS. 6a THROUGH 6d — DETAILED LOGIC DIAGRAM

FIGS. 6a through 6d illustrate a preferred embodiment of the circuit shown in FIG. 5, and set forth more specifically just how a circuit as shown in FIG. 5 may be constructed and operated. In viewing the drawings of FIG. 6, the drawings should be joined along the appropriate dotted lines in order to match adjoining portions of the circuitry.

Figure 6A:
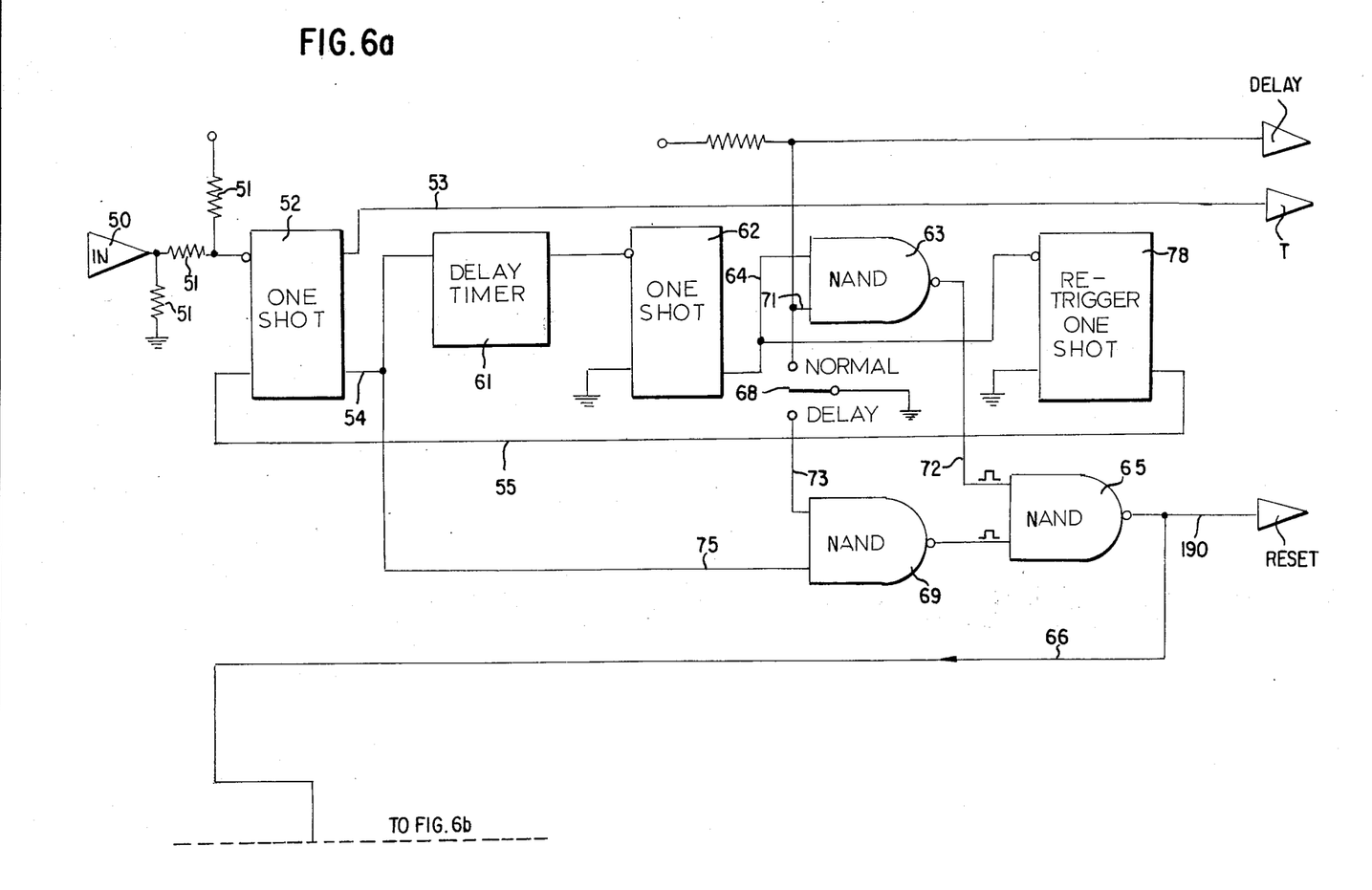
FIG. 6a to 6d are logic diagrams showing in more detail how the apparatus of FIG. 5 is constructed and operated.

Referring now to FIG. 6a, the "main bang" is received through a connector 50 and is reduced in power, so as to be compatible with the simulated circuitry by an arrangement of resistors 51. The "main bang" is applied to a one shot 52, which impresses trigger pulses over lines 53 and 54.

Figure 6B:
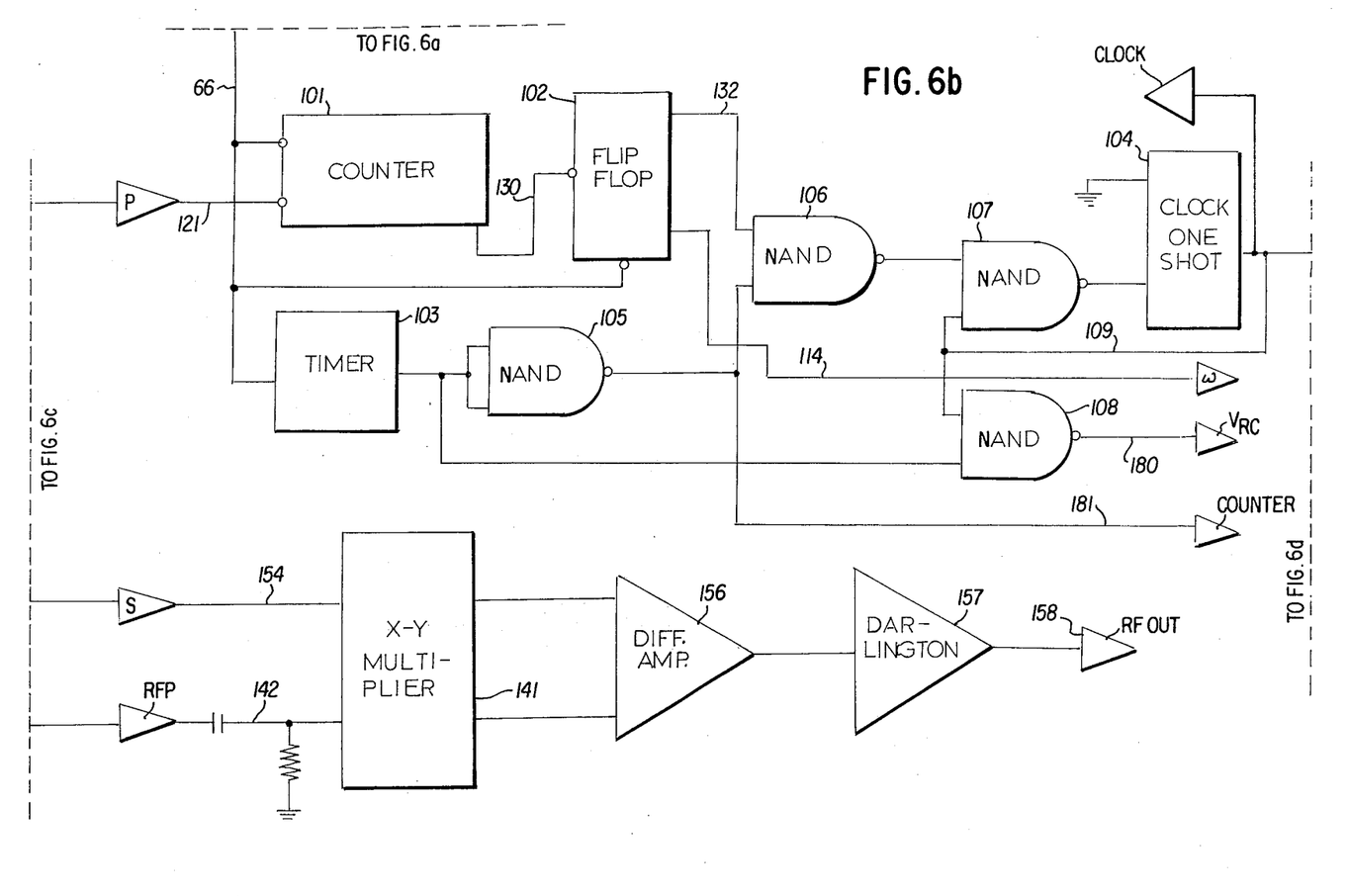
Figure 6C:
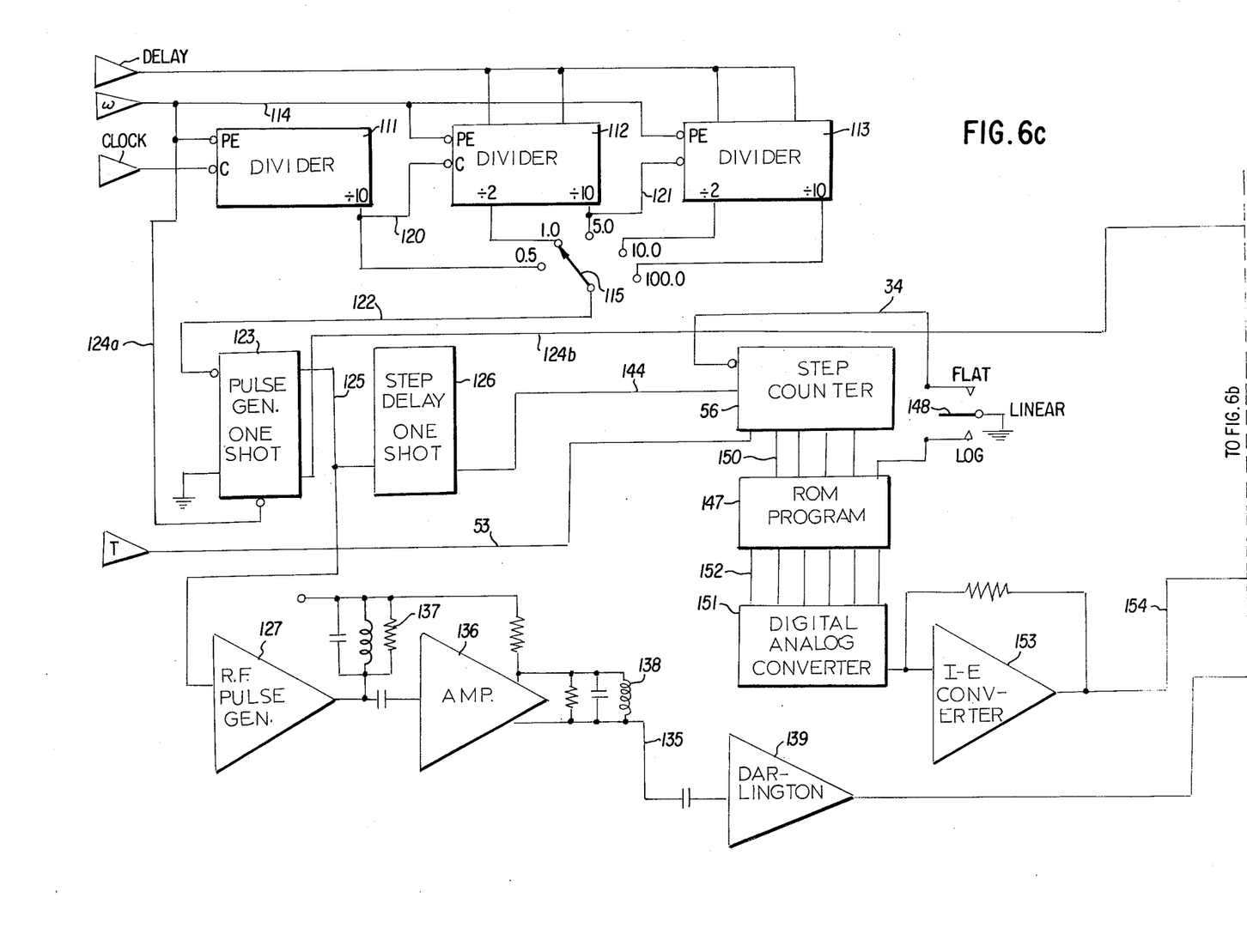

The trigger pulse over line 53 is applied to a step counter 56, which is part of the step generator 34 (see FIG. 6c). This resets the step generator 34 to step zero, so that it is able to begin operation as soon as the d.c. pulses of FIG. 1 are generated.

The pulse impressed over line 54 is either utilized immediately or is delayed by a delay timer 61, which is adjustable to introduce a delay of 12 to 45 microseconds. The delay timer 61 triggers a one shot 62 after the desired time interval has elapsed. The one shot 62 then pulses a NAND gate 63, which as explained hereinafter, pulses a NAND gate 65, which pulses line 66 and starts operation of the remainder of the simulator circuitry.

Selection between normal triggering in which the line 66 immediately receives a pulse and delayed triggering is accomplished by a switch 68, which grounds and inhibits either NAND gate 63 or an additional NAND gate 69. When the switch 68 is in the normal position, NAND gate 63 is inhibited, while NAND gate 69 is enabled. The pulses from one shot 52 are coupled through NAND gate 69 and NAND gate 65 to line 66. When switch 68 is in the delay position, NAND gate 69 is inhibited, while NAND gate 63 is enabled. The delayed pulses from one shot 62 are coupled through NAND gate 63 and NAND gate 65 to line 66.

Retrigger one shot 78 is a retriggerable one shot with a time interval considerably longer than the time between the "main bang" pulses from an ultrasonic flaw detector. As long as input pulses are being received, one shot 78 receives trigger pulses from one shot 62 and remains "on." However, if no input pulse is received for a period of approximately 0.2 seconds, one shot 78 turns "off" and in so doing triggers one shot 52 over line 55. The subsequent action is the same as when an input pulse is received. The retrigger one shot 78 enables the operator to set up the simulator without using a "main bang" from an ultrasonic flaw detector.

To summarize the circuitry of FIG. 6a, the line 66 is pulsed either immediately upon receiving the "main bang" pulse, or after being delayed 12 to 45 microseconds by the delay timer 61. When no input is present, the retrigger one shot 78 operates.

Referring to FIG. 6*b*, the pulse from line 66 is applied to set a counter 101, a flip flop 102, and to initiate action of a timer 103. Counter 101 counts the output pulses and resets flip flop 102 after the 11th pulse. Timer 103 generates a 100 microsecond pulse which times the count for the velocity display, the operation of which will be explained later.

One shot 104 together with NAND gate 107 make up the clock circuit, which is adjustable over a range of about 1.1 to 2.6 Megahertz by the velocity control. The clock is turned on and off by NAND gate 106. When the pulse from line 66 sets flip gate flop 102 and triggers timer 103, NAND gate 106 and the clock are turned on. The clock continues to run until timer 103 has timed out (100 microseconds) and flip flop 102 has been reset by counter 101 counting the 11th output pulse. When both of these actions have been completed, NAND gate 106 and the clock are turned off to await receipt of another trigger pulse.

The output from the clock one shot 104 is then applied to the frequency divider of FIG. 6*c*, which consists of three dividers 111, 112 and 113. These dividers are readied for operation by a pulse applied over the line 114 from flip flop 102. The frequency dividers 111, 112 and 113 are coordinated to divide the frequency of the clock one shot according to the thickness of the material under test by the position of a frequency selector switch 115. The frequency dividers 111, 112 and 113 are cascaded, so that the output from frequency 111 is connected over line 120 to frequency divider 112, and the output of frequency divider 112 is applied to the frequency divider 113 over line 121. Frequency divider 111 has one output in which its input frequency is divided by ten, while frequency dividers 112 and 113 both have two outputs in which their input frequencies are divided either by 2 or by 10. As previously set forth, the pulse repetition frequency of the final signal, which is applied to the ultrasonic flaw detector is inversely proportional to the thickness of the material being simulated.

In operation, if it is desired to simulate a material which is 0.5 inches thick, the selector switch 115 is set on the 0.5 setting, and the divider 111 divides the frequency by 10. If it is desired to simulate a material which is 1 inch thick, the thickness selector switch 115 is set on 1.0, so that the signal from the divider 111, impressed over line 120, is further divided by two. If, for example, it is desired to simulate a material which is 50 inches thick, the thickness selector switch 115 is set on 50 and the signal from the clock one shot is divided by 10 in the divider 111, by 10 in the divider 112, and again by 10 in the divider 113.

The output of the clock one shot, which has been divided by the frequency dividers, passes through the thickness selector switch 115, and is impressed along line 122 to energize a pulse generator one shot 123. The pulse generator one shot 123 has a single output pulse for each negative going transition of the signal received from the frequency dividers. The pulse generator 123 is also enabled for operation by a signal impressed over a line 114, and applied by a line 124*a*. There are two outputs from the pulse generator one shot 123. One output is impressed over line 124*b* to the counter 101, while the other output is impressed over a line 125 to a step delay one shot 126 and a radio frequency pulse generator 127. Referring now to FIG. 6*b*, the pulses applied over line 124*b* are counted by the counter 101, which counts eleven pulses and resets flip flop 102 as explained earlier. An output from flip flop 102 is impressed on line 114. This is a pulse which starts on receipt of the pulse on line 66 and ends when the eleventh output pulse has been generated. It enables dividers 111, 112 and 113 and pulse generator one shot 123 for its duration.

Line 181 carries a 100 microsecond pulse from the timer which turns off the LED display during the time a new count is being made.

Line 180 carries clock pulses for the 100 microsecond interval that the timer is on, after which NAND gate 108 is inhibited and no further clock pulses are permitted to reach line 180. These are the pulses which are counted for the VELOCITY display, as will be explained later.

Referring now, again, to FIG. 6*c*, the radio frequency pulse generator 127 applies a radio frequency pulse to a line 135 each time the pulse generator one shot 123 pulses line 125. The radio frequency pulse is then configured to resemble a gamma-type transducer pulse by suitable circuitry, which includes an amplifier 136 and resonant circuits 137 and 138. The damping in resonant circuits 137 and 138 electrically simulate the mechanical damping of the transducer being simulated. The radio frequency pulse on line 135 is amplified by a Darlington 139, and thereafter applied to an X–Y multiplier 141 by line 142.

In order to achieve the pulse envelope configurations of FIGS. 2, 3 and 4, it is necessary to modulate the amplitude of the radio frequency pulses received by the X–Y multiplier 141. This is accomplished by the step generator 34, shown in FIG. 6*c* Each pulse from the pulse generator one shot 123 applied over the line 125 is slightly delayed by the step delay one shot 126, in order to allow transmission of the RF pulse before stepping the gain of the X–Y multiplier to the next level. The output from step delay one shot 126 is applied over line 144 to the step counter 56 in the step generator 34. The step counter 56 is, in turn, connected to a read only memory 147, which contains a program for determining the amplitude of each radio frequency pulse registered in the X–Y multiplier 141. The selector switch 148 determines whether the pulses will have a constant amplitude as shown in FIG. 2, a linearly declining amplitude is shown in FIG. 3 or a logarithmically declining amplitude as shown in FIG. 4.

In operation, the step counter 56, in essence, sequences as it receives each pulse from the line 144 to address a new location in the read only memory. The lines 150 schematically illustrate the output from the step counter 56, and connect the step counter 56 to the read only memory 147. In the read only memory, the stored programs generate a multiplicand for each step which corresponds to the amplitude of the desired pulse. Using FIG. 3 as an example, the first pulse will have a multiplicand of one, which gives a full screen pulse; the second step will have a multiplicand of nine tenths, which gives a pulse which is nine tenths full screen; and the third step will have a multiplicand of eight tenths, which gives the pulse of eight tenths full screen. This reduction in amplitude continues until the 11th pulse when, again, the multiplicand has a value of one, so as to produce a full screen pulse. The 11th full screen pulse is to indicate the end of the pulse train.

The read only memory 147 has a digital output, which must be converted to an analog output, in order to be compatible with the X-Y multiplier 141. This is accomplished by a digital analog converter 151, which is connected to the read only memory by lines 152. Each signal from the digital analog converter is processed through an I-E converter 153, and applied to the X-Y multiplier 141 over a line 154.

The X-Y multiplier modulates the signal from the radio frequency pulse generator 127 according to the output from step generator 34 and applies the result through a differential amplifier 156 and Darlington 157 to the RF output connector 158, and then to the ultrasonic flaw detector. This, of course, is the signal which simulates the material under test in combination with the transducer of the ultrasonic flaw detector.

Figure 6D:
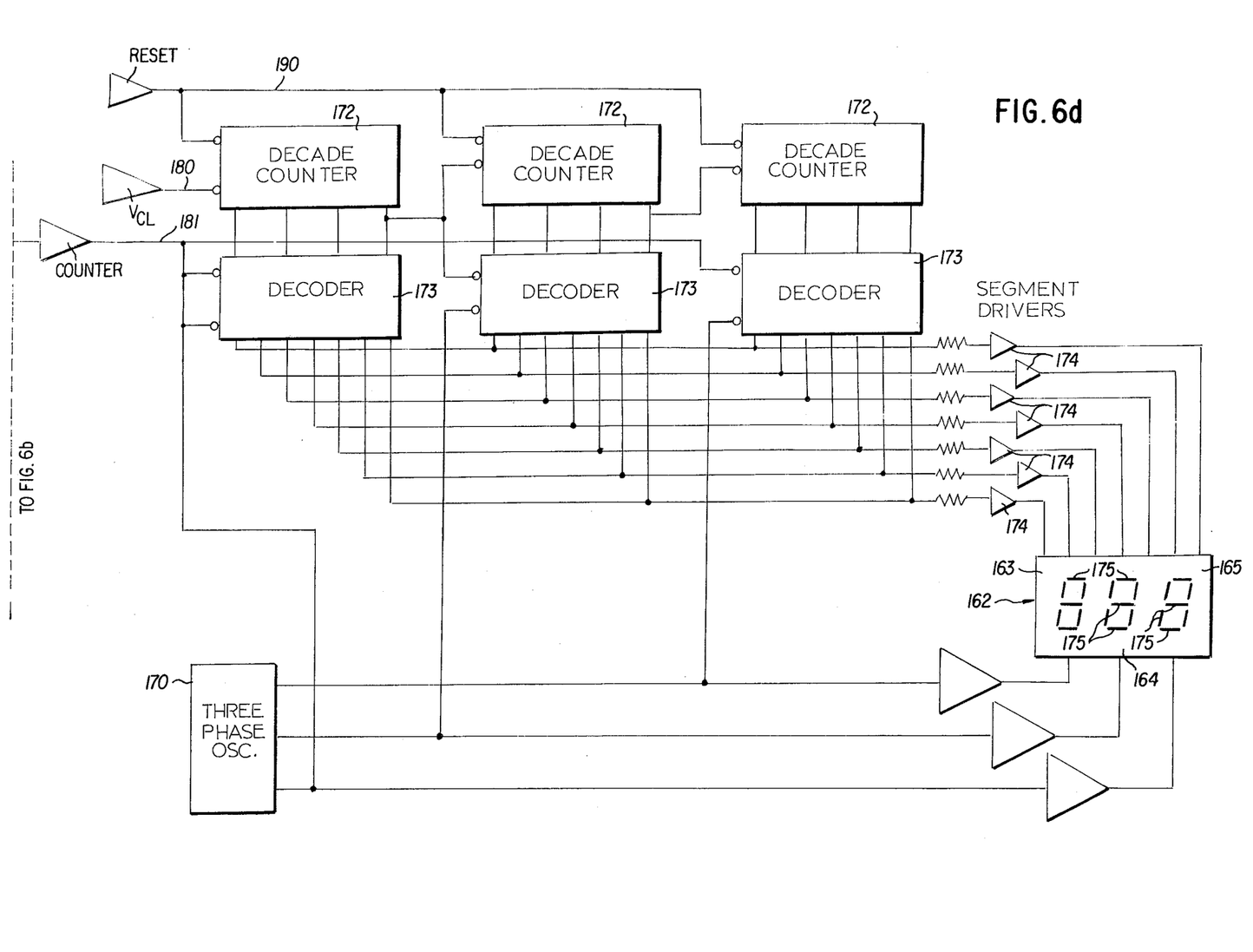

Referring now to FIG. 6d, there is shown a velocity display 162, which is preferably a light emitting diode type of display having three channels 163, 164 and 165. The indicator 162 is driven by a three-phase oscillator 170, which sequentially addresses and illuminates channels 163, 164 and 165. Associated with each channel is a decade counter 172 and decoder 173, which pulse segment drivers 174 in order to light the seven segments 173, associated with each digit of the indicator 162. The clock, which is gated onto line 180 as described earlier, is counted by the decade counters during the 100 microsecond timer interval. The indicator 162 is blanked during this count interval by the pulse on line 181. At the end of the count period, the three most significant figures of the clock frequency are displayed by the indicator.

Each decade counter 172 is reset upon operation of NAND gate 65 of FIG. 6a, which impresses a pulse over line 190 simultaneously with impressing a pulse over line 66.

By the afore-described structure, the appliant has embodied apparatus for simulating the combination of a transducer and a material under test, in order to calibrate and test ultrasonic flaw detectors. The applicant's invention, however, is defined by and should be limited only by the following claims.

What is claimed is:

1. A method of simulating an ultrasonic signal corresponding to a material under test in order to test circuitry of an ultrasonic test set, comprising the steps of:
   generating an initial pulse,
   generating a train of d.c. pulses in response to said initial pulse, the pulse repetition frequency of the d.c. pulses being inversely proportional to the thickness of the material being simulated and directly proportional to the speed of sound in the material being simulated,
   generating a radio frequency pulse with each d.c. pulse to produce a series of radio frequency pulses having a pulse repetition frequency of the d.c. pulses,
   shaping each radio frequency pulse to resemble those generated by an ultrasonic transducer; and
   modulating the amplitude of successive radio frequency pulses to produce a series of radio frequency pulses, which are selectively equal in amplitude, linearly declining in amplitude, or logarithmically declining in amplitude.

2. The method of claim 1 further including the step of stopping the pulses, after a predetermined number have been generated to await another initial pulse to start the series anew.

3. The method of claim 2 further including the step of: delaying between generating the initial pulse and generating the train of d.c. pulses, in order to simulate a material immersed in a liquid.

4. Apparatus for simulating an electrical signal produced by an ultrasonic transducer monitoring a material said apparatus comprising:
   means for applying an input pulse to said apparatus to initiate operation of said apparatus,
   clock means for generating a train of d.c. pulses the frequency of which is directly proportional to the speed of sound of the material,
   frequency dividing means for dividing the frequency of the train of d.c. pulses to produce an output the frequency of which is inversely proportional to the thickness of the material,
   radio frequency pulse generating means driven at the pulse repetition frequency of the frequency dividing means to produce a train of radio frequency pulses,
   means for shaping each radio frequency pulse to resemble those generated by an ultrasonic transducer,
   means for modulating the train of pulses from the radio frequency pulse generator to selectively produce trains of radio frequency pulses, which are equal in amplitude, linearly declining in amplitude, and logarithmically declining in amplitude, and
   means for applying said radio frequency pulses to said circuit under test.

5. The apparatus of claim 4 including means for counting said pulses and means for stopping said clock means after a predetermined number of pulses to thereby produce an identical radio frequency pulse train in response to each input pulse.

6. The apparatus of claim 4 wherein said means for applying an input includes means for delaying application of said input pulse to simulate the material being immersed in a liquid.

7. The apparatus of claim 4 further including indicating means for visually displaying the speed of sound of the material.

8. The apparatus of claim 4 wherein the means for modulating the train of pulses includes a step counter, a read only memory and a selection means for determining the amplitude of the radio frequency pulses.

9. A method of simulating an ultrasonic signal corresponding to a material under test in order to test set, said method comprising the steps of:
   generating an initial pulse,
   generating a train of d.c. pulses in response to said initial pulse, wherein said d.c. pulses have a pulse repetition frequency, which is directly proportional to the speed of sound in the material,
   dividing the frequency of the d.c. pulses by a factor proportional to the thickness of the material to produce a subsequent train of d.c. pulses having a pulse repetition frequency inversely proportional to the thickness of the material,
   generating a radio frequency pulse with each pulse of the subsequent train to produce a series of radio frequency pulses having the pulse repetition frequency of the subsequent train of pulses,
   shaping each radio frequency pulse to resemble those generated by an ultrasonic transducer, and
   modulating the amplitude of successive radio frequency pulses to produce a series of radio frequency pulses, which are selectively equal in amplitude, linearly declining in amplitude, or logarithmically declining in amplitude.

* * * * *